United States Patent

Sejpka et al.

Patent Number: 5,738,857
Date of Patent: Apr. 14, 1998

[54] COSMETIC COMPOSITIONS COMPRISING ORGANOSILOXANES

[75] Inventors: Johann Sejpka, Marktl; Annemarie Huber, Perach, both of Germany

[73] Assignee: Wacker-Chemie GmbH, Munich, Germany

[21] Appl. No.: 597,328

[22] Filed: Feb. 6, 1996

Related U.S. Application Data

[63] Continuation of Ser. No. 201,515, Feb. 24, 1994, abandoned.

[30] Foreign Application Priority Data

Mar. 2, 1993 [DE] Germany .................. 43 06 481.7

[51] Int. Cl.$^6$ ...................................... A61K 7/48
[52] U.S. Cl. ............. 424/401; 424/78.03; 424/70.121; 523/216; 524/730; 524/731
[58] Field of Search ............... 424/70.12, 70.121, 424/400, 401, 78.02, 78.03, 59; 514/63; 523/216; 524/730, 731; 556/431, 434, 444, 453, 459, 463, 465; 528/26, 29, 35, 37, 40

[56] References Cited

U.S. PATENT DOCUMENTS

| | | | |
|---|---|---|---|
| 3,632,619 | 1/1972 | Groenhof | 260/448.2 |
| 4,423,041 | 12/1983 | Clum et al. | 424/184 |
| 4,425,364 | 1/1984 | Vanlerberghe et al. | 424/358 |
| 4,855,129 | 8/1989 | Steinbach et al. | 424/63 |

FOREIGN PATENT DOCUMENTS

| | | |
|---|---|---|
| 0133964 | 7/1990 | European Pat. Off. |
| 2136442 | 9/1984 | United Kingdom |

OTHER PUBLICATIONS

SPS TL 1026 KhP–D82, 1982 Kruptjov et al.

*Primary Examiner*—Neil S. Levy
*Attorney, Agent, or Firm*—Martin Connaughton

[57] ABSTRACT

Cosmetic compositions which comprise waxy organosiloxanes, which are solid at room temperature, of the formula $$R^1R_2Si\text{—}O\text{—}SiR_2R^1 \qquad (I),$$

in which

R can be identical or different and represents an alkyl radical having 1 to 4 carbon atoms and $R^1$ can be identical or different and represents a linear alkyl radical having at least 16 carbon atoms, volatile organosiloxanes chosen from the group comprising hexamethyldisiloxane, octamethylcyclotetrasiloxane, decamethylcyclopentasiloxane and mixtures thereof, and optionally other substances.

5 Claims, No Drawings

COSMETIC COMPOSITIONS COMPRISING ORGANOSILOXANES

The application is a continuation of application Ser. No. 08/201515, filed on Feb. 24, 1994, now abandoned.

FIELD OF THE INVENTION

The present invention relates to cosmetic compositions which comprise at least one waxy and at least one volatile organosiloxane, and to a process for their preparation.

BACKGROUND OF INVENTION

Cosmetic formulations comprising organosiloxanes for the treatment of hair, nails and skin are already known in many instances. For example, anhydrous homogeneous cosmetic agents which contain dimethylpolysiloxane and organosilane or organosiloxane having at least one —$SiR^1R^2O_{2/2}$ unit, in which $R^1$ represents an alkyl radical having 2 to 30 carbon atoms, an aryl radical or a trimethylsiloxy radical and $R^2$ represents an alkyl radical having 1 to 30 carbon atoms, are described in EP-B 0 133 964 (Revlon, Inc.; published on Jul. 4, 1990). Furthermore, an anti-tackifying agent which comprises a mixture of a liquid and a waxy organosilicon compound, the waxy component being stearoxydimethylsilane or distearoxydimethylsilane or dipolyoxyethylenedimethylsilane, is described in GB-A-2 136 442. However, such waxy stearoxy compounds have the disadvantage that, because of the reactive Si—O—C bonds, they often give rise in cosmetic formulations, in particular in aqueous formulations, to undesirable changes such as, in consistency.

SUMMARY OF INVENTION

The present invention relates to cosmetic compositions which comprise waxy organosiloxanes, which are solid at room temperature, of the formula $$R^1R_2Si-O-SiR_2R^1 \quad (I),$$

in which

R can be identical or different and represents an alkyl radical having 1 to 4 carbon atoms and $R^1$ can be identical or different and represents a linear alkyl radical having at least 16 carbon atoms, and volatile organosiloxanes chosen from the group comprising hexamethyldisiloxane, octamethylcyclotetrasiloxane, decamethylcyclopentasiloxane and mixtures thereof, and optionally other substances.

Room temperature in the context of this invention is to be understood as meaning a temperature of about 20° C.

Examples of the radical R are the methyl and ethyl radical and propyl and butyl radicals, the methyl radical being particularly preferred.

Examples of the radical $R^1$ are the n-hexadecyl radical, n-heptadecyl radical and n-octadecyl, eicosenyl and docosenyl radical, the n-octadecyl radical being particularly preferred.

In the context of the present invention, the radicals R and $R^1$ are to be combined in the organosiloxanes of the formula (I) only such that a waxy organosiloxane which is solid at room temperature results.

An exemplary organosiloxane of formula (I) is $H_{37}C_{18}Si(CH_3)_2-O-Si(CH_3)_2C_{18}H_{37}$.

Octamethylcyclotetrasiloxane and decamethylcyclopentasiloxane are preferably employed as the volatile organosiloxane, octamethylcyclotetrasiloxane being particularly preferred.

Organosiloxanes of the formula (I) and the volatile organosiloxanes mentioned are commercially available products and can be prepared by the processes customary in silicone chemistry.

In the compositions according to the present invention, the weight ratio of solid, waxy organosiloxane to volatile organosiloxane is preferably 1:999 to 2:3, more preferably 1:99 to 3:7, in particular 1:99 to 15:85.

The compositions according to the present invention can be used in any desired preparations for the treatment of skin, nails and hair. Examples of these are emulsions, such as cleansing emulsions, liquid nutrient creams, body lotions, sun screen agents and bath milk, creams, such as, solid creams of the type such as night creams, skin nutrient creams, sunscreen creams and the like, and sticks, such as deodorant sticks, lipsticks and eye make-up sticks.

The compositions according to the present invention are preferably preparations for treatment of the skin.

Depending on the field of use, the compositions according to the present invention can then comprise, in addition to the waxy organosiloxanes of formula (I) and the volatile organosiloxanes, other substances customary for formulation of cosmetic preparations.

Examples of additives which are employed optionally are animal, mineral, vegetable or synthetic oils, waxes or resins, wetting agents, fatty alcohols, emulsifiers, ultra violet (U.V.) absorbers, organic solvents, thickening agents, dyestuffs, pigments, pH regulators, reducing agents, electrolytes, clouding additives, preservatives, antioxidants, aqueous agents, perfumes, antiseborrheic agents and active compounds which can be used for treatment, care and protection of the skin or hair, and water.

The nature and amount of the additives employed optionally depend on the particular field of use and are extensively known in the cosmetics sector.

The compositions according to the present invention are preferably those which comprise a solid, waxy organosiloxane of formula (I) in amounts of preferably 0.1 to 40% by weight, particularly 3 to 10% by weight, more preferably 3 to 5% by weight, based on the total weight of the composition.

To prepare the compositions according to the present invention, the waxy organosiloxane of formula (I) and volatile organosiloxane and the substances added optionally are mixed with one another in any desired manner.

Advantageously, however, the waxy organosiloxane of formula (I) is first dissolved in the volatile organosiloxane and this solution is then mixed with additives, optionally.

The present invention furthermore relates to a process for the preparation of cosmetic compositions, which comprises dissolving a waxy organosiloxane, which is solid at room temperature, of formula (I) in a volatile organosiloxane chosen from the group comprising hexamethyldisiloxane, octamethylcyclotetrasiloxane, decamethylcyclopentasiloxane and mixtures thereof, and optionally mixing the resulting solution with other substances.

The process according to the present invention is preferably carried out at 20° to 70° C., more preferably 20° to 50° C., under a pressure of 900 to 1100 hPa. If desired, for better incorporation, any of the above referenced optional additives depending on their nature, can be heated themselves before being mixed with the solution of organosiloxane of formula (I) and volatile organosiloxane and then added at this temperature.

The process according to the present invention has the advantage that it is very easy to carry out and allows homogeneous distribution of the active compound.

The compositions according to the present invention have the advantage that the waxy organosiloxane of formula (I), which is a valuable active compound in connection with preparations for body care, is distributed homogeneously therein. Furthermore, the compositions have the advantage that they are very easy to apply and easy to distribute, and after evaporation of the volatile organosiloxanes, give a firmly adhering film which cannot be easily removed even by moisture or water and imparts a dry and non-tacky feel to the skin. The fact that the compositions are stable for a long period of time and, with respect to the organosiloxanes, do not change their consistency, is a further advantage.

In the examples described below, all the parts and percentages relate to the weight, unless stated otherwise. Furthermore, all the viscosity data relate to a temperature of 25° C. Unless stated otherwise, the following examples were carried out under a pressure of the surrounding atmosphere, that is at about 1000 hPa, and at room temperature, at about 20° C., or at a temperature which is established when the reactants are brought together at room temperature without additional heating or cooling.

The term "stearylsiloxane" in the following is to be understood as meaning a disiloxane of the formula $H_{37}C_{18}Si(CH_3)_2$—O—$Si(CH_3)_2C_{18}H_{37}$.

EXAMPLE 1

1.00 part of paraffin oil (commercially obtainable under the name "Paraffin oil, thin-bodied" from Merck, Darmstadt), 1.00 part of cetyl alcohol and 1.50 parts of stearic acid are mixed with one another at a temperature of 85° C. (mixture A).

1.50 parts of stearylsiloxane are dissolved in 4 parts of decamethylcyclopentasiloxane at a temperature of 50° C. (mixture B).

0.80 part of triethanolamine, 3.00 parts of 1,2-propanediol and 88.20 parts of water are mixed with one another at a temperature of 85° C. (mixture C).

Mixture B is stirred into mixture A, and mixture C is then added. Mixtures A, B and C are added at their individual preparation temperature. 0.05 g of isothiazolinone (commercially obtainable under the name "Kathon CG" from Rohm & Haas GmbH, Frankfurt) and 0.1 g of fragrance (commercially obtainable under the name "Synambran" from Wacker-Chemie GmbH, Munich) are also added to the formulation thus obtained and the mixture is allowed to cool to room temperature. A thick lotion results which is absorbed very rapidly into the skin and does not cause greasiness.

The lotion shows no change in consistency during storage at 45° C. under about 1000 hPa over a period of more than 10 weeks.

EXAMPLE 2

5.50 parts of candellila wax and 3 parts of stearic acid are mixed with one another at a temperature of 70° C. (mixture A).

6.70 parts of stearylsiloxane are dissolved in 18.30 parts of decamethylcyclopentasiloxane at a temperature of 50° C. (mixture B).

1.30 parts of triethanolamine, 3.40 parts of 1,2-propanediol and 44.80 parts of water are mixed with one another at a temperature of 70° C. (mixture C).

Mixture C is stirred into mixture A, and mixture B is then added. Mixtures A, B and C in each case are added at their individual preparation temperature. 14 g of titanium dioxide and 3 g of pigment (commercially obtainable under the name "Sicomet-Braun 70" from BASF, Ludwigshafen) are also added to the formulation thus obtained and the mixture is allowed to cool to room temperature. A creamy smooth masking cream with a very good covering power results. The masking cream shows no change in consistency during storage at 45° C. under about 1000 hPa over a period of more than 10 weeks.

EXAMPLE 3

1.00 part of stearylsiloxane is dissolved in 25 parts of octamethylcyclotetrasiloxane at a temperature of 50° C. (mixture A).

69 parts of paraffin oil (commercially obtainable under the name "Paraffin oil, thin-bodied" from Merck, Darmstadt) and 5 parts of polypropylene glycol 15-stearyl ether (commercially obtainable under the name "Arlamol E" from ICI, UK) are mixed with one another at a temperature of 20° C. (mixture B).

Mixture B is stirred into mixture A, at their respective preparation temperatures. 0.05 g of isothiazolinone (commercially obtainable under the name "Kathon CG" from Rohm & Haas GmbH, Frankfurt) and 0.2 g of fragrance (commercially obtainable under the name "Majantol" from Wacker-Chemie GmbH, Munich) are also added to the formulation thus obtained and the mixture is allowed to cool to room temperature. A colorless, clear, thin-bodied bath oil with re-oiling properties results.

The bath oil shows no change in consistency during storage at 45° C. under about 1000 hPa over a period of more than 10 weeks.

What is claimed is:

1. A cosmetic composition consisting essentially of, (A) a waxy organosiloxane, which is solid at room temperature, of the formula $$R^1R_2Si\text{—}O\text{—}SiR_2R^1 \qquad (I),$$

in which

R is identical or different and represents an alkyl radical having 1 to 4 carbon atoms and $R^1$ is identical or different and represents a linear alkyl radical having at least 16 carbon atoms, (B) a volatile organosiloxane chosen from the group consisting of hexamethyldisiloxane, octamethylcyclotetrasiloxane, decamethylcyclopentasiloxane and mixtures thereof, and (C) substances customary for formulation of cosmetic compositions selected from the group consisting of, animal, mineral, vegetable or synthetic oils, waxes or resins, wetting agents, fatty alcohols, emulsifiers, ultra violet (U.V.), absorbers, organic solvents, thickening agents, dyestuffs, pigments, pH regulators, reducing agents, electrolytes, clouding additives, preservatives, antioxidants, aqueous agents, perfumes, antiseborrheic agents and mixtures thereof.

2. A cosmetic composition as claimed in claim 1, wherein the organosiloxane of formula (I) is $H_{37}C_{18}Si(CH_3)_2$—O—$Si(CH_3)_2C_{18}H_{37}$.

3. A cosmetic composition as claimed in claim 1, wherein the volatile organosiloxane is octamethylcyclotetrasiloxane.

4. A cosmetic composition as claimed in claim 1, wherein the weight ratio of solid, waxy organosiloxane of formula (I) to volatile organosiloxane is 1:999 to 2:3.

5. A cosmetic composition as claimed in claim 1, wherein the solid, waxy organosiloxane of formula (I) is present in an amount of 0.1 to 40% by weight, based on the total weight of the composition.

* * * * *